United States Patent [19]

Badley et al.

[11] Patent Number: 5,989,926
[45] Date of Patent: Nov. 23, 1999

[54] RECOVERY OF AND USES OF SPECIFIC BINDING AGENTS

[75] Inventors: Robert A Badley, Bedford; Mark J Berry, Northampton; Philip Porter, Bedford; Trevor Wattam, Northampton, all of United Kingdom

[73] Assignee: Unipath Limited, Basingstoke, United Kingdom

[21] Appl. No.: 08/955,723

[22] Filed: Oct. 22, 1997

Related U.S. Application Data

[63] Continuation of application No. 08/562,589, Nov. 24, 1995, abandoned.

[30] Foreign Application Priority Data

Nov. 24, 1994 [EP] European Pat. Off. ............. 94308705

[51] Int. Cl.⁶ .................................................. G01N 33/533
[52] U.S. Cl. .................. 436/538; 435/7.1; 435/7.95; 435/961; 436/507; 436/510; 436/512; 436/518; 436/541; 436/547; 436/8; 436/16; 530/389.2
[58] Field of Search .................................... 435/7.1, 7.95, 435/961; 436/507, 510, 512, 518, 541, 547, 8, 16; 530/389.2

[56] References Cited

U.S. PATENT DOCUMENTS

| | | | |
|---|---|---|---|
| 4,952,569 | 8/1990 | Simons | 424/88 |
| 5,467,778 | 11/1995 | Catt et al. | 128/38 |
| 5,527,686 | 6/1996 | Fitzpatrick et al. | 435/7.9 |

FOREIGN PATENT DOCUMENTS

| | | | |
|---|---|---|---|
| 0 175 269 | 3/1986 | European Pat. Off. | C07K 1/00 |
| 0 324 540 | 7/1989 | European Pat. Off. | G01N 33/78 |
| 0 383 313 A3 | 8/1990 | European Pat. Off. | G01N 33/74 |
| WO 85/01941 | 5/1985 | WIPO | C07G 7/00 |
| WO 91/05262 | 4/1991 | WIPO | G01N 33/543 |
| WO 95/00174 | 1/1995 | WIPO | A61K 39/395 |

OTHER PUBLICATIONS

Voet et al. Biochemistry, pp. 90–92, 1990.

*Primary Examiner*—James C. Housel
*Assistant Examiner*—Bao-Thuy L. Nguyen
*Attorney, Agent, or Firm*—Pillsbury Madison & Sutro LLP

[57] ABSTRACT

An antibody specific for a target analyte is purified by affinity chromatography on a substrate bearing a low-affinity analogue of the target analyte. The antibody is displaced from the substrate by contact with a second analogue of intermediate affinity, which remains complexed with the antibody. This complex can be used in a conventional assay for the target analyte, which displaces the intermediate-affinity analogue. The complexed antibody is rendered more storage-stable because the second analogue protects the antibody binding reagion.

11 Claims, 2 Drawing Sheets

RECOVERY OF AND USES OF SPECIFIC BINDING AGENTS

This is a continuation of application Ser. No. 08/562,589, filed on Nov. 24, 1995 which was abandoned.

FIELD OF THE INVENTION

This invention relates to processes for the recovery of and uses of specific binding agents.

BACKGROUND TO THE INVENTION

The need for assay systems which are faster and more efficient has lead to a desire for specific binding agents which have higher affinities with respect to a target ligand. The production and selection of high affinity specific binding agents is not technically difficult; this can be achieved by hybridoma technology or the use of non-mammalian cells such as bacteria which have been modified by genetic engineering to express a specific binding protein. However, the effective recovery of the specific binding agent from the medium (generally a cell culture medium) into which it has been expressed remains an area in which there is considerable room for improvement.

Selective precipitation of the specific binding agent, which is normally a protein such as an immunoglobulin, carries the considerable risk that the protein will be denatured and hence the desired properties of the specific binding agent will be reduced or lost altogether. Affinity purification, in which the desired specific binding agent is selectively adsorbed onto a solid phase material and subsequently eluted, is an alternative. A highly efficient way of extracting the desired specific binding agent from the cell culture medium is to expose the medium to a solid phase, such as a column, onto which is immobilised the target ligand against which the specific binding agent has been raised. However, this results in the specific binding agent becoming very strongly adsorbed onto the solid phase, and the elution procedure necessary to recover it involves extreme conditions such as the use of strong buffers which again are very likely to damage the sensitive reagent. To some extent this risk of damage can be reduced by employing on the solid phase an analogue of the target ligand which is selected such that the specific binding agent has a substantially lower affinity for the analogue than it does for the target ligand. As a result the specific binding agent is less strongly adsorbed onto the solid phase and the elution conditions required to remove it are less severe.

GENERAL DESCRIPTION OF THE INVENTION

The present invention provides a much improved method for recovering high affinity specific binding agents in active form. The invention uses the known principle of selective adsorption of the specific binding agent onto a solid phase bearing an immobilised analogue of the target ligand. However, subsequent retrieval of the specific binding agent is achieved by exposing the solid phase to a medium containing a second analogue of the target ligand, the affinity of the specific binding agent for the second analogue being of intermediate magnitude. Due to the reversible nature of specific binding reactions, when the solid phase onto which the high affinity specific binding agent has been adsorbed is in the presence of the medium-affinity second analogue, the specific binding agent is progressively released from the solid phase into the medium and binds preferentially to the second analogue. By choosing appropriate affinities for the first and second analogues, the complex formed between the specific binding agent and the second analogue will itself dissociate readily in the presence of the target ligand and the target ligand will bind preferentially to the specific binding agent. Thus the complex formed between the specific binding agent and the second analogue can be used for example in assays intended to detect the target ligand, in the same manner as a conventional uncomplexed specific binding agent. Moreover, if desired, the displacement of the second analogue can be used as part of the assay result detection system, for example by having a detectable label attached to the second analogue.

A further and highly important benefit associated with the invention is that we have found that the complex formed between the specific binding agent and the second analogue greatly assists in maintaining the functional stability of the specific binding agent. The reasons for this are not fully understood, but possibly this enhanced stability arises because the analogue is occupying the active binding site of the specific binding agent and protects this is critical site against damage. The invention therefore provides a very efficient way of recovering high affinity specific binding agents and of stabilising such agents prior to use.

In one embodiment, the invention provides a process for recovering a specific binding agent possessing high affinity for a target ligand, in which process:

a) a first medium containing the specific binding agent is contacted with a solid phase bearing immobilised thereon a first analogue for the target ligand, said specific binding agent possessing comparatively low affinity for said first analogue;

b) following separation of the solid phase from said first medium, said solid phase is contacted with a second medium containing a second analogue for the target ligand, said specific binding agent possessing an intermediate affinity for said second analogue, whereby specific binding agent which has become bound to said solid phase is preferentially bound to said second analogue and thereby released from said solid phase in the form of a complex with said second analogue, but from which complex said second analogue can be displaced by exposure to said target ligand in bindable form.

Preferably the affinity of said specific binding reagent for said target ligand is at least about 5 times, more preferably at least about 20 times, and most preferably at least about 100 times greater than its affinity for said first analogue.

Preferably the affinity of said specific binding reagent for said target ligand is at least about 5, and more preferably at least about 10 times greater than its affinity for said second analogue.

Examples of specific binding agents to which the invention can be applied are antibodies or antibody fragments, such as $Fab_2$, Fab or FV fragments. Said second analogue can be an epitope mimic, i.e. a small molecule, generally of synthetic origin, such as a short peptide, which behaves in a manner comparable to the binding site (epitope) of the target ligand.

As set out in the accompanying example, the invention can be applied advantageously when said target ligand is estradiol or a metabolite thereof, such as estrone-3-glucuronide (E3G). Especially when the target ligand is E3G, said first analogue can be estrone. Preferably said second analogue is estriol glucuronide. Alternatively, estradiol-3-glucuronide can be used as the second analogue; in this case, estriol-3-glucuronide may optionally be used as the first analogue.

The invention also provides a reagent comprising a specific binding agent for a target ligand, said specific binding agent being complexed with an analogue of said target ligand, the affinity of said specific binding agent for said analogue being substantially less than its affinity for said target ligand such that, when said complex is exposed to said target ligand in bindable form (i.e. the relevant epitope of the target ligand is free to engage in complex formation with the specific binding agent), said target ligand displaces said analogue from said complex and preferentially binds to said specific binding agent.

The following Examples serve merely as illustrations of the invention.

EXAMPLES

Examples 1 to 7 describe the recovery and analysis of a monoclonal antibody (and its corresponding Fv fragment) raised against the steroid hormone estrone-3-glucuronide. The chemical structure of estrone-3-glucuronide, and the analogues used in these Examples, are shown in FIG. 1. Also shown is the extent to which the analogues cross-react with the monoclonal antibody. Details of how to generate cross-reactivity data are given in Gani et al (1994).

BRIEF DESCRIPTION OF THE DRAWINGS

In the accompanying drawings.

I: Estrone beta-D-glucuronide ("Estrone-3-glucuronide") also known as 1,3,5[10]-Estratrien-3-ol-17-one 3-glucuronide; or 3-Hydroxy-1,3,5[10]-estratrien-17-one 3-glucuronide.

II: 17beta-Estradiol 3-(beta-D-glucuronide) also known as 1,3,5[10]-Estratrien-3,17beta-diol 3-glucuronide; or 3,17beta-Dihydroxy-1,3,5[10]-estratriene 3-glucuronide.

III: Estriol 3-(beta-D-glucuronide) also known as 1,3,5 [10]-Estratrien-3,16alpha, 17beta-triol 3-glucuronide; or 3,16alpha, 17beta-Trihydroxy-1,3,5[10]-estratriene 3-glucuronide. 0.7% Cross Reactive with I.

IV. Estrone, also known as 1,3,5[10]-Estratrien-3-ol-17one; or 3-Hydroxy-1,3,5[10]-estratrien-17-one. 0.1% Cross Reactive with I.

Figure 1:
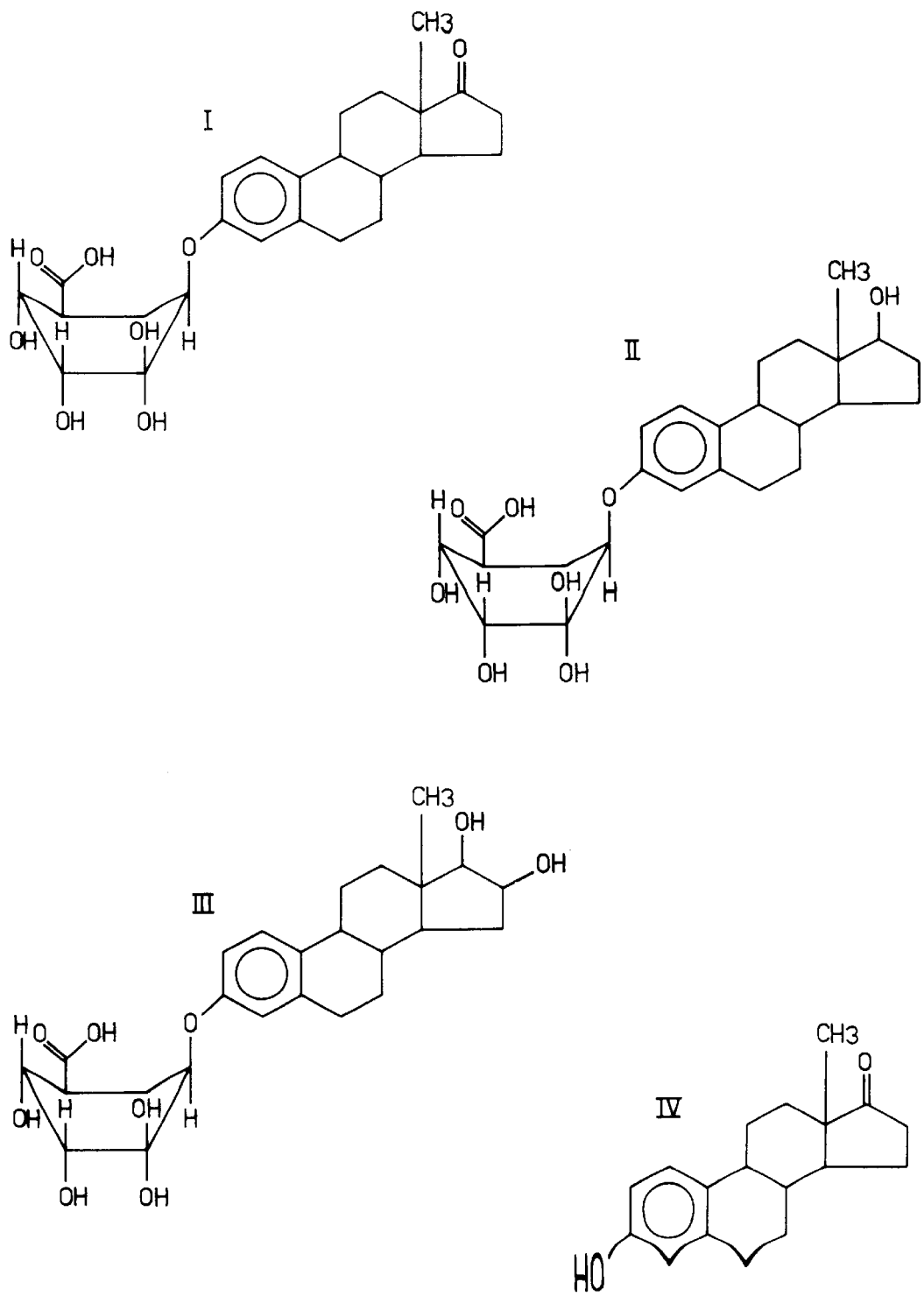
FIG. 1 depicts structural formulae of four metabolites used in the following examples, namely.
Figure 2:
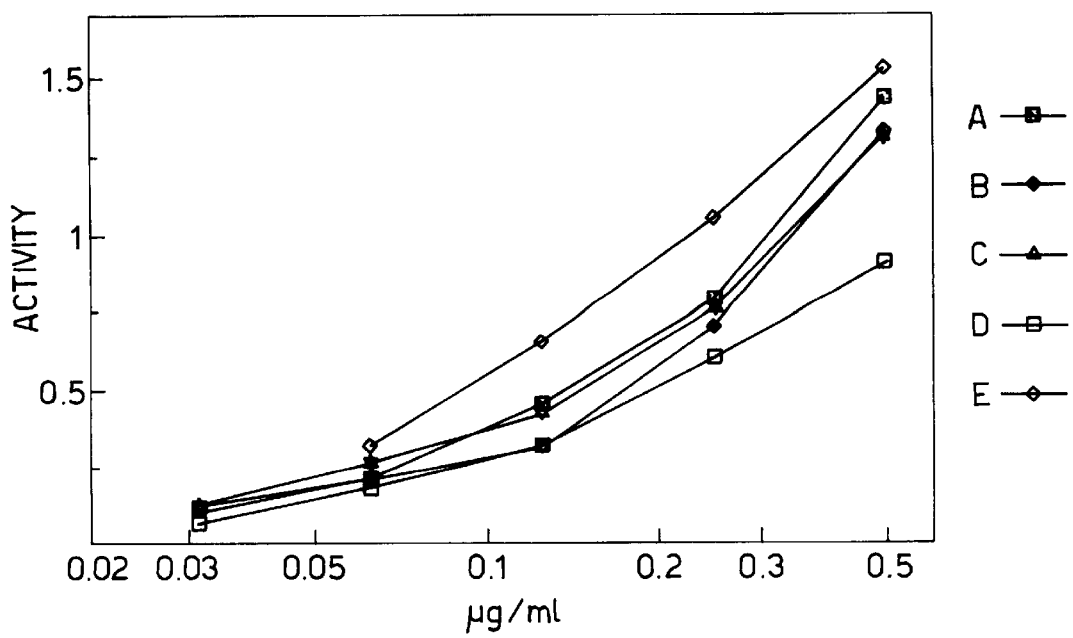

FIG. 2 compares the specific activities, expressed as absorbance at 450 nm, of various antibody fractions (see Example 4).

Figure 3:
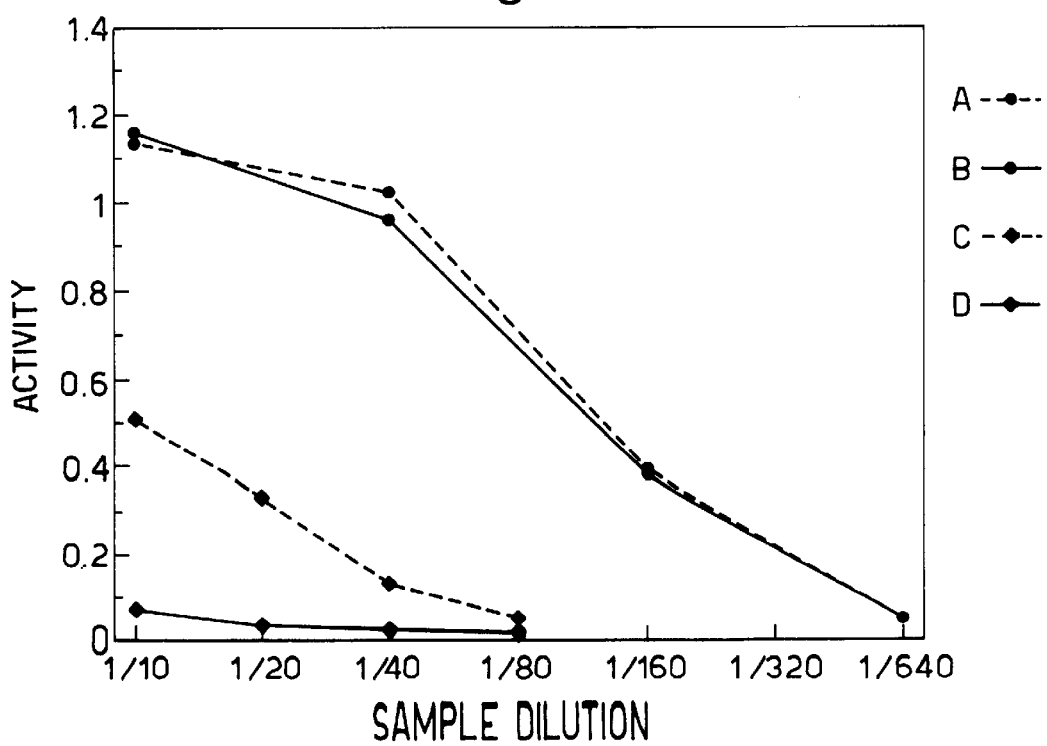

FIG. 3 compares the retention of specific activity, again expressed as absorbance at 450 nm, during storage of an antibody prepared in accordance with the invention and one prepared by conventional means (see Example 7).

EXAMPLE 1

Synthesis of Estrone-agarose Affinity Column

The hydroxyl group on estrone was coupled to a chromatography medium which had been derivatised with epoxy groups (Pharmacia epoxy 6B Sepharose) according to the protocol below:

i) 3 g of epoxy 6B Sepharose [Pharmacia] was weighed out into a 200 ml glass beaker. 200 mls of MilliQ water was added, and the gel was left to resuspend for 30 minutes.

ii) 4.3 mg of estrone [Sigma] was weighed out into a sterile glass universal. This was dissolved in 5 mls of HPLC grade dimethylformamide (DMF) [Aldrich].

iii) The Sepharose was collected together in a P16 sinta glass using a vacuum pump and flask, care being taken not to dry out the Sepharose. It was then washed with a further 600 mls of MilliQ water, followed by 100 mls of 85% DMF/15% MilliQ water.

iv) The Sepharose was carefully added to the estrone solution. Residual Sepharose in the sinta glass was washed out with additional 85% DMF in MilliQ. The volume in the universal was then increased to 25 mls with 85% DMF in MilliQ.

v) 7 μl of 10M NaOH was added to the solution and the pH checked using a glass pH probe to confirm that the pH was 13+.

vi) The glass universal was then placed in a 45° C. incubator with slow rotation for at least 16 hours.

vii) The Sepharose was again collected with a P16 sinta glass and washed with 200 ml of 85% DMF in MilliQ, followed by 400 mls of PBS.

viii) The Sepharose was packed in a C16 column [Pharmacia] and stored at 40° C. until required.

EXAMPLE 2

Recovery of a Monoclonal Antibody (MAB) Specific for Estrone-3-glucuronide from Cultured Media Hybridoma cells producing a monoclonal antibody (MAB) specific for estrone-glucuronide were grown up in culture medium according to standard techniques. This feedstock was clarified by centrifugation and then applied to the estrone affinity column prepared in Example 1. Unbound protein was removed by washing the column with phosphate-buffered saline [0.01M $Na_2HPO_4$–$NaH_2PO_4$/ 0.15M NaCl (pH7)]. Bound MAB was desorbed with 10 mls of an 0.7 mg/ml solution of estradiol-glucuronide in phosphate-buffered saline. The recovered MAB was passed down a gel filtration column (G-25 Sephadex, Pharmacia) to remove excess (ie. unbound) estradiol-glucuronide. This procedure would not be expected to remove estradiol-glucuronide that was bound to the MBA.

EXAMPLE 3

Determination of MAB Activity by ELISA i) Microtitre plates were sensitised with estrone-glucuroide by incubating wells with a 2 μg/ml solution of an ovalbumin/estrone-glucuronide conjugate in carbonate buffer (0.2M $Na_2CO_3$/$NaHCO_3$, pH 9.6). Sensitisation was overnight at 37° C. Instructions on how to synthesise protein/steroid conjugates are given in Gani et al (1994).

ii) Sensitised plates were aspirated and rinsed three times with PBST [Phosphate-buffered saline containing 0.15% tween 20 (Sigma)]. MAB-containing samples were diluted i PBST and then applied to sensitised plates at a range of dilutions. Each plate was incubated for 1 hour at room temperature.

iii) Plates were washed with PBST as above, and then incubated with a 1/1000 dilution of a goat anti-mouse/ alkaline phosphatase conjugate (Zymed) for 1 hour at room temperature.

iv) Plates were washed with PBST and then incubated with a 1 mg/ml solution of para-nitrophenolphosphate (Sigma) made up in substrate buffer (50 mM diethylamine; pH 9.8, with 1 mM $MgCl_2$). Plates were incubated at room temperature until colour development had occurred (usually about 1 hour). Signal was measured at 405 nm.

EXAMPLE 4
Comparison of Specific Activities of Different MAB Preparations

A MAB preparation, which had been affinity-purified according to the invention (as described in Example 2), had its specific activity compared with that of four MAB batches which had been purified by conventional technology, i.e. on a protein A column Goding (1980) and Hale et al (1994).

Each MAB preparations was diluted out to a range of concentrations (as determined by optical density at 280 nm—taking an extinction coefficient of 1.4) and then analysed by the protocol described in Example 3.

Specific activity (the activity per unit of protein) is given by the steepness of the curves in FIG. 2. It is clear that the MAB preparation purified according to the invention (line E in FIG. 2) has a higher specific activity than the four preparations purified by conventional technology (lines A to D).

EXAMPLE 5
Recovery of an Fv Antibody Fragment Specific for Estrone-glucuronide from Cultured Media An Fv specific for estrone-glucuronide and tagged at the C-terminus of its $V_L$ chain with the myc peptide was produced in *E. coli* according to the method of Ward et al (1989). This feedstock was clarified by centrifugation and then passing through an 0.2 $\mu$m filter unit (Nalgene). The clarified feedstock was applied to an estrone affinity column (as described in Example 1). Unbound Fv was removed by washing the column with phosphate-buffered saline. Bound Fv was eluted with 10 mls of an 0.2 mg/ml solution of estrol glucuronide (made up in phosphate-buffered saline). The recovered Fv was passed down a gel filtration column (G-25 Sephadex, Pharmacia) to remove excess (i.e. unbound) estriol glucuronide. This procedure would not be expected to remove estriol glucuronide which had bound to the Fv.

This experiment was repeated with the same volume of the same Fv-containing feedstock. This time, bound Fv was eluted with a conventional buffer for removing Fv from affinity columns, pH 2 buffer as described in King et al (1993).

EXAMPLE 6
Determination of Fv Activity by ELISA i) Microtitre plates were sensitised with estrone-glucuronide by incubating wells with a 2 $\mu$g/ml solution of an ovalbumin/estrone-glucuronide conjugate made up in carbonate buffer, pH 9.6. Sensitisation was overnight at 37° C.

ii) Sensitised plates were aspirated and rinsed three times with PBST [Phosphate buffered saline containing 0.15% Tween 20 (Sigma)]. Fv-containing samples were diluted in PBST and then applied to sensitised plates at a range of dilutions. The plate was incubated for 1 hour at room temperature.

iii) Plates were washed with PBST as above and then incubated with a 2.6 $\mu$g/ml solution of anti-myc MAB made up in PBST, as described in Ward et al (1989). Plates were incubated for 1 hour at room temperature.

iv) Plates were washed with PBST and then incubated with a 1/1000 dilution of anti-mouse/alkaline phosphatase conjugate (Zymed) for 1 hour at room temperature.

v) Plates were washed with PBST and then incubated with a 1 mg/ml solution of para-nitrophenolphosphate (Sigma) made up in substrate buffer (50 mM diethylamine, pH 9.8, 1 mM $MgCl_2$). Plates were incubated at room temperature until colour development had occurred (usually about 1 hour). Signal was measured at 405 nm.

EXAMPLE 7
Comparison of the Activity and Stability of Fv Produced by the Technology of the Invention With That of Fv Produced by Conventional Means The activity of Fv prepared by elution with estriol glucuronide was compared with Fv eluted with pH2 buffer. This was done by analysing the two preparations (made in Example 5) with the assay procedure described in Example 6.

The stability of these two fractions was also compared by storing aliquots of each preparation at 40° C. and at 37° C. It was assumed that the Fv was stable at 4° C. and that any inactivation at 37° C. would be measured relative to this base-line. The risk of bacterial contamination was minimised by sterile-filtering each aliquot prior to storage and taking a fresh aliquot for each analysis.

The results after 18 days of storage are shown in FIG. 3. Specific activity is shown at various dilutions. Line A is the analogue-eluted Fv reagent of the invention after 18 days storage at 4° C., and line B after 18 days storage at 37° C. Lines C and D show the activity of the same Fv reagent produced by elution with pH 2 buffer, again after storage for 18 days at 4° C. (line C) and 37° C. (line D). It is clear that Fv produced in accordance with the invention is several-fold more active and that it is also more stable at 37° C.

References

M Gani et al (1994) *J. Steroid Biochem. Molec. Biol.* Vol 48. No 2/3 p277–282

J W Goding (1980) *J. Immuno Methods.* 39 p285–308

G Hale et al (1994) *J. Immuno Methods* 171 p 15–21

D J King et al (1993) *Biochem. J.* 290 p723–729

E S Ward et al (1989) *Nature* 341, p 544–546

We claim:

1. A process for recovering a specific binding agent possessing high affinity for a target ligand which comprises:
   (a) contacting a first medium containing the specific binding agent with a solid phase having immobilized thereon a first analogue of the target ligand, said specific binding agent possessing comparatively low affinity for said first analogue when compared with the affinity of said binding agent to the target ligand or a second analogue of said target ligand;
   (b) separating the solid phase from said first medium;
   (c) then contacting said solid phase with a second medium containing said second analogue of the target ligand, said specific binding agent possessing an intermediate affinity for said second analogue which is greater than the affinity of said first analogue for said binding agent but less than the affinity of said target ligand for said binding agent, whereby specific binding agent which has become bound to said solid phase is preferentially bound to said second analogue and thereby released from said solid phase in the form of a complex with said second analogue and subsequently displacing said second analogue from said complex by exposure of said complex to said target ligand wherein the specific binding agent preferentially binds to said target ligand.

2. A process according to claim 1, wherein the affinity of said specific binding agent for said target ligand is at least about 5 times greater than its affinity for said first analogue.

3. A process according to claim 2, wherein the affinity of said specific binding agent for said target ligand is at least about 5 times greater than its affinity for said second analogue.

4. A process according to claim 1, wherein said specific binding agent is an antibody or antibody fragment.

5. A process according to claim 1, wherein said second analogue is an epitope mimic.

6. A process according to claim 1, wherein said target ligand is estradiol or a metabolite thereof, especially estrone-3-glucuronide (E3G).

7. A process according to claim 6, wherein said target ligand is E3G and said first analogue is estrone.

8. A process according to claim 7, wherein said second analogue is estriol-3glucuronide or estradiol-3-glucuronide.

9. The process of claim 2 wherein the affinity of the binding agent for said target ligand is at least about 10 times greater than its affinity for said first analogue.

10. The process of claim 2 wherein the affinity of the binding agent for said target ligand is at least about 100 times greater than its affinity for said first analogue.

11. A process according to claim 2, wherein the affinity of said specific binding agent for said target ligand is at least about 10 times greater than its affinity for said second analogue.

* * * * *